(12) United States Patent
McConnell et al.

(10) Patent No.: US 11,541,068 B2
(45) Date of Patent: *Jan. 3, 2023

(54) HMO COMPOSITIONS AND METHODS FOR REDUCING AUTISM SPECTRUM DISORDER SYMPTOMS

(71) Applicant: Glycom A/S, Hørsholm (DK)

(72) Inventors: Bruce McConnell, La Tour de Peilz (CH); Louise Kristine Vigsnæs, Copenhagen (DK)

(73) Assignee: Glycom A/S, Hørsholm (DK)

( * ) Notice: Subject to any disclaimer, the term of this patent is extended or adjusted under 35 U.S.C. 154(b) by 406 days.

This patent is subject to a terminal disclaimer.

(21) Appl. No.: 16/616,374

(22) PCT Filed: May 24, 2018

(86) PCT No.: PCT/IB2018/053676
§ 371 (c)(1),
(2) Date: Nov. 22, 2019

(87) PCT Pub. No.: WO2018/215961
PCT Pub. Date: Nov. 29, 2018

(65) Prior Publication Data
US 2020/0101094 A1    Apr. 2, 2020

(30) Foreign Application Priority Data

May 24, 2017    (DK) .......................... PA 2017 70380

(51) Int. Cl.
  *A61K 31/702*    (2006.01)
  *A61P 1/00*    (2006.01)
  *A61P 25/00*    (2006.01)
(52) U.S. Cl.
  CPC .............. *A61K 31/702* (2013.01); *A61P 1/00* (2018.01); *A61P 25/00* (2018.01)
(58) Field of Classification Search
  CPC .... A61K 31/702; A61K 31/22; A61K 31/716; A61K 2300/00; A61P 1/00; A61P 25/00; C08B 37/00; C08L 5/00
  USPC .......................................................... 514/54
  See application file for complete search history.

(56) References Cited

U.S. PATENT DOCUMENTS

| | | | |
|---|---|---|---|
| 2012/0171165 A1 | 7/2012 | Buck et al. | |
| 2012/0172319 A1* | 7/2012 | Chow ...................... | A23L 33/12 514/54 |
| 2013/0195803 A1 | 8/2013 | German et al. | |
| 2013/0243139 A1 | 9/2013 | Tomita | |
| 2016/0113952 A1 | 4/2016 | Dekany | |
| 2016/0213697 A1 | 7/2016 | Fallon et al. | |
| 2016/0243139 A1 | 8/2016 | Vigsnæs et al. | |
| 2016/0287637 A1* | 10/2016 | McConnell ............ | A61K 35/20 |
| 2016/0339065 A1* | 11/2016 | Adams ................... | A61K 35/74 |

FOREIGN PATENT DOCUMENTS

| | | | |
|---|---|---|---|
| EP | 2091526 | 6/2008 | |
| EP | 2888950 A1 | 1/2015 | |
| EP | 2888950 A1 | 7/2015 | |
| WO | 01/04341 A1 | 1/2001 | |
| WO | 2007101862 A1 | 9/2007 | |
| WO | 2010115934 A1 | 10/2010 | |
| WO | 2010115935 | 10/2010 | |
| WO | 2011100979 A1 | 8/2011 | |
| WO | 2011100980 | 8/2011 | |
| WO | 2012007588 A9 | 1/2012 | |
| WO | 2012113404 A1 | 8/2012 | |
| WO | 2012113405 A1 | 8/2012 | |
| WO | 2012127410 A1 | 9/2012 | |
| WO | 2012155916 A1 | 11/2012 | |
| WO | 2012156897 A1 | 11/2012 | |
| WO | 2012156898 A1 | 11/2012 | |
| WO | WO 2013/032674 A1 * | 3/2013 | ........... A61K 31/702 |
| WO | 2013044928 A1 | 4/2013 | |
| WO | 2013091660 A1 | 6/2013 | |
| WO | 2013139344 A1 | 9/2013 | |
| WO | 2015100091 A1 | 7/2015 | |
| WO | 2016/063262 A1 | 4/2016 | |
| WO | 2016063262 A1 | 4/2016 | |
| WO | 2017/046711 A1 | 3/2017 | |
| WO | 2017/156550 A1 | 9/2017 | |

OTHER PUBLICATIONS

Gotham et al, Autism, 2015, 19(4), 491-504.*
Spilioti et al, Frontiers in Neuroscience, 2013, 7, 1-7.*
Herbert et al, Journal of Child Neurology, 2013, 28(8), 975-982.*
Pieper et al, Animal Health Research Reviews, 2016, 17(2), 137-147.*
Wang et al., Dig Dis Sci, 2012, 57, 2096-2102.*
M. Chichlowski, et al., "Bifidobacteria isolated from infants and cultured on human milk oligosaccharides affect intestinal epithelial function", J Pediatr Gastroenterol Nutr., Sep. 2012, pp. 1-17.
F. Bottacini, et al., "Diversity, ecology and intestinal function of bifidobacteria", 11th International Symposium on Lactic Acid Bacteria Egmond aan Zee, the Netherlands, Aug. 31-Sep. 4, 2014, pp. 1-15.
A. Kindworth et al., Evaluation of general 16S ribosomal RNA gene PCR primers for classical and next-generation sequencing-based diversity studies, Nucleic Acids Research, 2013, vol. 41, No. 1, Aug. 28, 2012, pp. 1-11.
S. Duranti et al., "Exploration of the Genomic Diversity and Core Genome of the Bifidobacterium adolescentis Phylogenetic Group by Means of a Polyphasic Approach", Applied and Environmental Microbiology vol. 79 No. 1, Jan. 2013, pp. 336-346.

(Continued)

*Primary Examiner* — Ganapathy Krishnan
(74) *Attorney, Agent, or Firm* — Kunzler Bean & Adamson; Tom Briscoe

(57) ABSTRACT

The invention relates to human milk oligosaccharides (HMO) and its use in treatment of autism spectrum disorder (ASD).

20 Claims, 1 Drawing Sheet

(56) References Cited

OTHER PUBLICATIONS

Xi Chen, "Human Milk Oligosaccharides (HMOS): Structure, Function, and Enzyme-Catalyzed Synthesis" Advances in Carbohydrate Chemistry and Biochemistry, vol. 72, 2015, pp. 113-190.
L. Bode, "Human milk oligosaccharides and their beneficial effects", Handbook of dietary and nutritional aspects of human breast milk, Human Health Handbooks No. 5, 2013, pp. 515-531.
T. Urashima et al., "Milk Oligosaccharides", Nova Biomedial Books, 2011, pp. 1-99.
RC Edgar, "UPARSE: highly accurate OTU sequences from microbial amplicon reads", Nature Methods vol. 10 No. 10, Oct. 2013, pp. 996-1000.
C. Villodre et al., "Down-regulation of monocarboxylate transporter 1 (MCT1) gene expression in the colon of piglets is linked to bacterial protein fermentation and pro-inflammatory cytokine-mediated signalling", British Journal of Nutrition (2015), 113, Feb. 6, 2015, pp. 610-617.
L. Wang et al., "Elevated Fecal Short Chain Fatty Acid and Ammonia Concentrations in Children with Autism Spectrum Disorder", Dig Dis Sci, Springer, Apr. 3, 2012, pp. 1-7.
"Information From European Union Institutions, Bodies, Offices and Agencies European Commission", Official Journal of the European Union, Nov. 25, 2017, pp. 1-15.
R. Pieper, Health relevance of intestinal protein fermentation in young pigs', Animal Health Research Reviews 17 (2);, Aug. 30, 2016, pp. 137-147.
Ht Ding, "Gut Microbiota and Autism: Key Concepts and Findings", J Autism Dev Disord, Springer, 2016, pp. 1-10.
E. Elison et al., "Oral supplementation of healthy adults with 2!-O-fucosyllactose and lacto-N-neotetraose is well tolerated and shifts the intestinal microbiota", British Journal of Nutrition (2016), 116, Oct. 10, 2016, pp. 1356-1368.
18806174.1, "Extended European search report", EPO, dated Jan. 25, 2021, pp. 1-9.
R. Grimaldi et al., "A prebiotic intervention study in children with autism spectrum disorders (ASDs)", Microbiome, Biomed Central Ltd., vol. 6, No. 1, Aug. 2, 2018, pp. 1-13.
R. Grimaldi et al., "In vitro fermentation of B-GOS: impact on faecal bacterial populations and metabolic activity in autistic and non-autistic children", FEMS Mictrobiology Ecology, vol. 93, No. 2, Nov. 16, 2016, pp. 1-10.
PCT/IB2018/053676, Notification of Transmittal of the International Search Report and the Written Opinion of the International Searching Authority, or the Declaration, dated Aug. 14, 2018, pp. 1-22.
Monique Haarman et al., "Quantitative Real-Time PCR Assays To Identify and Quantify Fecal Bifidobacterium Species in Infants Receiving a Prebiotic Infant Formula", Biomedical Research Department, Microbiology Section, Numico Research BV, 2004 vol. 71, No. 5, Nov. 30, 2004, pp. 1-7.

\* cited by examiner

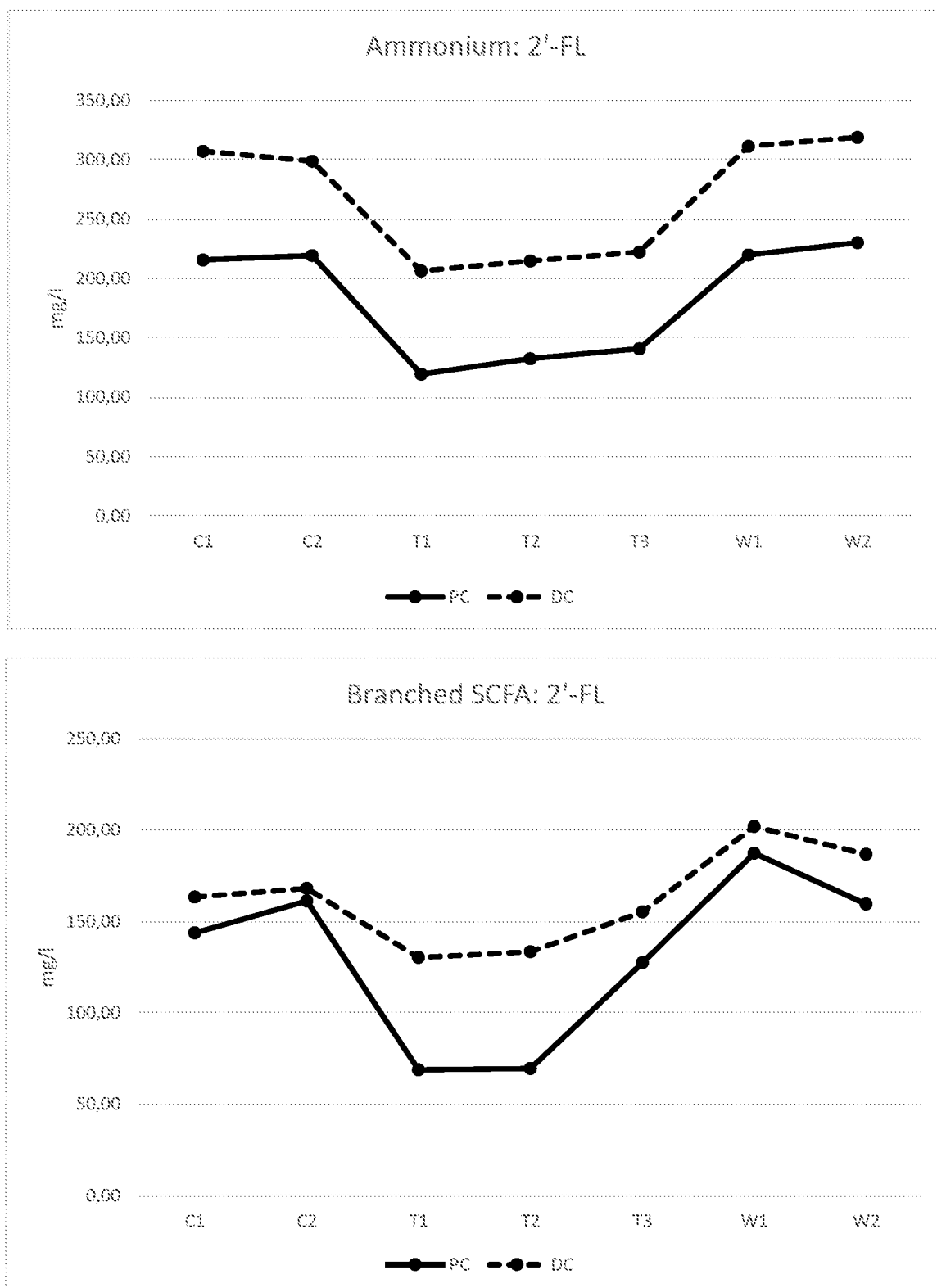

HMO COMPOSITIONS AND METHODS FOR REDUCING AUTISM SPECTRUM DISORDER SYMPTOMS

FIELD OF THE INVENTION

This invention relates to methods of managing and/or treating autism spectrum disorder (ASD).

BACKGROUND TO THE INVENTION

The autism spectrum is a range of complex conditions classified as neurodevelopmental disorders. Disorders include autism, Asperger syndrome, pervasive developmental disorder not otherwise specified, and childhood disintegrative disorder. Individuals diagnosed with an autism spectrum disorder (ASD) must present two types of symptoms:
  deficits in social communication and social interaction; and
  restricted, repetitive patterns of behaviour, interests or activities.

ASD typically appears during the first three years of life and manifests in characteristic symptoms or behavioural traits. One course of development occurs gradually over the first two years of life and diagnosis is made around 3-4 years of age. Some of the early signs of ASDs in this course include decreased looking at faces, failure to turn when name is called, failure to show interests by showing or pointing, and delayed pretend play. A second course is characterized by normal or near-normal development followed by loss of skills or regression in the first 2-3 years. Regression may occur in a variety of domains, including communication, social, cognitive, and self-help skills; however, the most common regression is loss of language.

In addition to the characteristic ASD symptoms, ASD individuals display a wide range of neurological comorbidities, including intellectual disability, epilepsy, and anxiety and mood disorders. They also commonly display non-neurological comorbidities, including blood hyperserotonaemia, immune dysregulation, and gastrointestinal dysfunction (e.g., chronic constipation, diarrhoea, abdominal pain, and gastroesophageal reflux).

To date, there are no approved medications for reducing or eliminating the core symptoms of ASD. The only two approved medications are specifically indicated for reducing irritability in subjects having ASD. Consequently, treatment is often focussed on lessening associated deficits and family distress, and to increase quality of life and functional independence. Many methods adopt a psychoeducational approach to enhancing cognitive, communication, and social skills while minimizing problem behaviours. In particular, the American Academy of Paediatrics (AAP) has proposed new recommendations emphasizing early involvement with both developmental and behavioural methods, support by and for parents and caregivers, and a focus on both the core and associated symptoms of ASD.

A recent hypothesis on the aetiology of ASD links the condition to changes in the intestinal microbiota. This hypothesis arises in part from the close connection between ASD and gastrointestinal symptoms indicative of dysbiosis of the intestinal microbiota. Also, it has been observed that the onset of neurobehavioral symptoms and chronic diarrhoea appears to occur after repeated courses of antibiotics in a subset of children with the regressive form of ASD. A species of toxin-producing *Clostridium* was proposed as a possible cause (Ding et al. *J. Autism Dev. Disord.* 47, 480 (2017)). This *Clostridium* hypothesis is further supported by a study in which children with regressive autism were treated with a 6-week course of oral vancomycin, an antibiotic with known activity against clostridia. Significant improvement in neurobehavioral symptoms was observed in eight of the ten children studied as well as improvement in gastrointestinal symptoms.

Another potential link between ASD and the intestinal microbiota relates to ammonia concentrations in the gastrointestinal tract and in circulation. Protein that enters the large intestine non-digested, promotes putrefactive fermentation and selective growth of proteolytic bacteria such as members of *Fusobacteria, Streptococcaceae, Megasphera, Selenomonas, Bacteroidetes, Proteobacteria* and putatively pathogenic species such as *E. coli, Klebsiella* spp., *Campylobacter* spp., *Streptococcus* spp., *C. perfringens*, and *C. difficile*. When protein is utilized by these bacteria, branched short chain fatty acids (B-SCFA), ammonia, amines and phenolic compounds are produced, some of which are potentially harmful to human health (Pieper et al. Anim. Health Res. Rev. 17, 137 (2016).

Ammonia in particular can interfere with the oxidative metabolism of butyrate in colonocytes, inducing energy deficiency, increased apoptosis and higher proliferation. This negatively impacts the physical and functional integrity of the colonic mucosa by altering mucin gene and tight junction expression. In particular, it is believed that ammonia and other protein-derived metabolites such as B-SCFA present in the lumen negatively influence the expression of monocarboxylate transporter 1 (MCT1) (Villodre et al. Brit. J. Nutr. 113, 610 (2015)). MCT1 is stimulated by butyrate leading to increase butyrate uptake by colonocytes. The inhibition of MCT1 by high concentration of protein-derived metabolites in the intestine can impair the protective effect of butyrate on the colon epithelium and lead to pro-inflammatory conditions in the colon.

Normally, gut-derived ammonia is taken up by the liver and consumed in the urea cycle and passes out of the body in urine. However, altered intestinal permeability can increase the amount of ammonia delivered to the liver causing liver saturation making the liver inefficient in processing the ammonia. The ammonia is then returned to the blood for circulation. High concentration of ammonia in the blood can cause damage to the liver and affect the central nervous system such as impairing intracerebral synthesis of serotonin and dopamine and producing abnormal neurotransmitters such as octopamine. Higher concentrations of faecal ammonia have been reported in children with autism spectrum disorders (43 mmol/g faeces) compared with control children (32 mmol/g faeces) (Wang et al. *Dig. Dis. Sci.* 57, 2096 (2012)).

Human milk oligosaccharides (HMOs) are a heterogeneous mixture of soluble glycans found in human milk. They are the third most abundant solid component after lactose and lipids in human milk and are present in concentrations of 5-25 g/l (Bode, in: *Handbook of dietary and nutritional aspects of human breast milk* (Zibadi et al. eds.), 515-31, Wageningen Academic Publishers (2013)). HMOs are resistant to enzymatic hydrolysis in the small intestine and are thus largely undigested and unabsorbed. The majority of HMOs that reach the colon serve as substrates to shape the gut ecosystem by selectively stimulating the growth of specific saccharolytic bacteria. HMOs are believed to substantially modulate the infant gut microbiota and play a decisive role in the differences in the microbiota of formula-fed and breast-fed infants. These differences include the predominance of the saccharolytic bifidobacteria in the gut of breast-fed infants compared to a more diverse gut microbiota in formula-fed infants. This is viewed as beneficial for the infant because strains of *Bifidobacterium* species are believed to have a positive effect on gut health (Chichlowski et al. *J. Pediatr. Gastroenterol. Nutr.* 55, 321 (2012)). HMOs are also able to increase the abundance of bifidobacteria in adults (Elison et al. *Brit. J. Nutr.* 116, 1356 (2016)).

US patent application 2016/0213697 describes the use of lactulose in the treatment of autism. Lactulose is a non-absorbable sugar generally used to treat constipation and hyperammonaemia. When used to treat hyperammonaemia, relatively large doses need to be taken 3 to 4 times a day. This causes episodic diarrhoea; often requiring the users to wear diapers and plastic pants.

International patent application WO 2015/100091 describes the use of 2'-fucosyl-lactose in the treatment of neuroinflammation as a means of treating or reducing cognitive impairment.

There remains a need for a safe, well tolerated, means of reducing in ASD patients the concentration of proteolytic metabolites such as ammonia in the gastrointestinal tract and in circulation. Further, remains a need for a safe, well tolerated, means of improving gastrointestinal function in ASD patients.

SUMMARY OF THE INVENTION

In a first aspect, this invention provides a human milk oligosaccharide, advantageously a neutral human milk oligosaccharide, for use in:
  decreasing the concentration of proteolytic metabolites, such as ammonia and branched short chain fatty acids, in the gastro-intestinal tract of an autism spectrum disorder (ASD) patient;
  reducing gastrointestinal symptom severity in an ASD patient;
  improving gut barrier function in an ASD patient, and/or
  decreasing autism spectrum symptom severity in an ASD patient.

In one embodiment, the HMO is for use in:
  decreasing the concentration of proteolytic metabolites, such as ammonia and branched short chain fatty acids, in the gastro-intestinal tract of an autism spectrum disorder (ASD) patient;
  reducing gastrointestinal symptom severity in an ASD patient; and/or
  improving gut barrier function in an ASD patient.

A second aspect of the invention is a synthetic composition comprising a human milk oligosaccharide, advantageously a neutral human milk oligosaccharide, for use in:
  decreasing the concentration of proteolytic metabolites, such as ammonia and branched short chain fatty acids, in the gastro-intestinal tract of an ASD patient;
  reducing gastrointestinal symptom severity in an ASD patient;
  improving gut barrier function in an ASD patient and/or
  decreasing autism spectrum symptom severity in an ASD patient.

In one embodiment, the synthetic composition is for use in:
  decreasing the concentration of proteolytic metabolites, such as ammonia and branched short chain fatty acids, in the gastro-intestinal tract of an autism spectrum disorder (ASD) patient;
  reducing gastrointestinal symptom severity in an ASD patient; and/or
  improving gut barrier function in an ASD patient.

The synthetic composition can be a nutritional or pharmaceutical composition. The synthetic composition may further comprise a ketogenic compound. Preferably, the ketogenic compound is a medium chain triglyceride and/or a ketone body such as a hydroxybutyrate ester, for example D-β-hydroxybutyrate-(R)-1,3-butanediol monoester ((R)-3-hydroxybutyl (R)-3-hydroxybutyrate).

A third aspect of this invention is a method for decreasing the concentration of proteolytic metabolites, such as ammonia and branched short chain fatty acids, in the gastrointestinal tract of an ASD patient, the method comprising orally or enterally administering to the patient an effective amount of a human milk oligosaccharide, advantageously a neutral human milk oligosaccharide. Preferably, the HMO is administered for a period of at least 14 days.

A fourth aspect of this invention is a method for reducing gastrointestinal symptom severity in an ASD patient, the method comprising orally or enterally administering to the patient for an effective amount of a human milk oligosaccharide, advantageously a neutral human milk oligosaccharide. Preferably, the gastrointestinal symptom severity is reduced by at least 20% as assessed by the Gastrointestinal Symptom Rating Scale (GSRS) relative to severity as assessed prior to administration of the human milk oligosaccharide, advantageously a neutral human milk oligosaccharide. Preferably, the HMO is administered for a period of at least 14 days.

A fifth aspect of this invention is a method for improving gut barrier function in an ASD patient, the method comprising orally or enterally administering to the patient an effective amount of a human milk oligosaccharide, advantageously a neutral human milk oligosaccharide. Preferably, the HMO is administered for a period of at least 14 days.

The human milk oligosaccharide can be administered with a ketogenic compound or as part of a ketogenic diet. Preferably, the ketogenic compound is a medium chain triglyceride and/or a ketone body such as a hydroxybutyrate ester, for example D-β-hydroxybutyrate-(R)-1,3-butanediol monoester ((R)-3-hydroxybutyl (R)-3-hydroxybutyrate).

Preferably the concentration of ammonia in the colon is decreased by at least 10% as compared to concentrations prior to HMO administration; more preferably by at least 20%. The concentration of branch short chain fatty acids in the colon is preferably decreased by at least 10% as compared to concentrations prior to HMO administration; more preferably by at least 20%. Further, the concentration of butyrate in the proximal colon is preferably increased by at least 50%; more preferably by at least 100%, after 14 days.

A sixth aspect of the invention is a method for decreasing autism spectrum symptom severity in an ASD patient, the method comprising administering to the patient for at least 7 days an effective amount of one or more human milk oligosaccharides, advantageously a neutral human milk oligosaccharide, to decrease the concentration of proteolytic metabolites, such as ammonia and branched short chain fatty acids in the gastro-intestinal tract of the patient. Preferably, the one or more human milk oligosaccharides are administered for at least 14 days to increase butyrate levels in the gastro-intestinal tract of the patient.

Preferably, the autism spectrum symptom severity of the patient improves by at least 10% compared to before treatment.

Preferably, the level of butyrate in the gastro-intestinal tract of the ASD patient increases by at least 100% compared to the level prior to HMO administration; more preferably at least 200%.

A seventh aspect of the invention is a use of
- one or more human milk oligosaccharides (HMOs), advantageously a neutral HMO,
- a synthetic composition comprising one or more human milk oligosaccharides (HMOs), advantageously a neutral HMO, or
- a pack comprising at least 7 individual daily doses of an effective amount of one or more human milk oligosaccharides, advantageously a neutral HMO, in the dietary management of an ADS patient.

An eighth aspect of the invention is a pack for use in decreasing autism spectrum symptom severity in an ASD patient, the pack comprising at least 7 individual daily doses of an effective amount of one or more human milk oligosaccharides, advantageously a neutral HMO. Preferably, each dose contains about 1 g to about 20 g of the human milk oligosaccharide, more preferably about 2 g to about 10 g, for example about 3 g to about 7.5 g. Preferably, the pack comprises at least 14 individual daily doses; more preferably at least 21 daily doses, for example at least 28 daily doses. The pack can include instructions for use. The individual daily doses may include a ketogenic compound as described above.

In all aspects disclosed above, preferably, the neutral HMO is a fucosylated neutral HMO, such as 2'-FL, 3-FL or DFL, or a mixture thereof, a non-fucosylated neutral HMO, such as LNnT or LNT, or a mixture thereof, especially a mixture of a fucosylated and a non-fucosylated neutral HMO.

BRIEF DESCRIPTION OF THE FIGURES

FIG. 1 illustrates the effect of 2'-FL on branched B-SCFA and ammonia production (mg/l) in the proximal (PC) and distal (DC) colon reactor. Samples were taken during two control weeks (C), three treatment weeks (T) and two washout weeks (W), for metabolic analysis.

DETAILED DESCRIPTION OF THE INVENTION

It has now been surprisingly found that administration of human milk oligosaccharides (HMOs) to autism spectrum disorder patients decreases the concentration of detrimental or proteolytic metabolites such as ammonia and branched chain fatty acids in the gastro-intestinal tract of these patients. This in turn may reduce the concentration of ammonia in circulation. Human milk oligosaccharides, by oral or enteral ingestion, dynamically modulate the intestinal microbiota by preferentially promoting the growth of bifidobacteria, for example bifidobacteria of the *Bifidobacterium adolescentis* phylogenetic group, *Bifidobacterium longum* and/or *Bifidobacterium bifidum*. This increases the abundance of this/these bacteria in the colon and reduces detrimental and/or proteolytic metabolites in the colon. The more beneficial microbial community in the intestine improves gastrointestinal symptoms. Further, administration of the HMO for a period of at least 14 days results in an increase in butyrate in the colon of the patient. The increase in butyrate improves the gastrointestinal barrier by providing a source of energy for colonocytes in the epithelial layer.

The reduction in detrimental and/or proteolytic metabolites can result in a detectable improvement in one or more indicators or symptoms of ASD including changes in eye tracking, skin conductance and/or electroencephalography (EEG) measurements in response to visual stimuli, difficulties engaging in and responding to social interaction, verbal and nonverbal communication problems, repetitive behaviours, intellectual disability, difficulties in motor coordination, attention issues, sleep disturbances, and physical health issues such as gastrointestinal disturbances.

"Autism spectrum symptom severity" or "ASD symptom severity" means the severity of ASD symptoms as assessed by autism testing tools such as the Childhood Autism Rating Scale (CARS), the Childhood Autism Rating Scale 2-Standard Form (CARS2-ST), the Childhood Autism Rating Scale 2-High Functioning (CARS2-HF), the Aberrant Behaviour Checklist (ABC), the Social Responsiveness Scale (SRS), and/or the Vineland Adaptive Behaviour Scale II (VABS-II).

"Gastrointestinal symptom severity" or "GI symptom severity" means the severity of gastrointestinal symptoms as assessed by tools such as the Gastrointestinal Symptom Rating Scale (GSRS).

"Ketogenic compound" means a compound which is a ketone or a ketone precursor which may be converted or metabolised in the body into a ketone. Ketogenic compounds include medium chain triglycerides, hydroxybutyrates and their derivatives; for example esters of hydroxybutyrate and oligomers of hydroxybutyrate. An especially preferred ketogenic compound medium chain triglycerides or D-β-hydroxybutyrate-(R)-1,3-butanediol monoester ((R)-3-hydroxybutyl (R)-3-hydroxybutyrate), or both.

"Human milk oligosaccharide" or "HMO" means a complex carbohydrate found in human breast milk (Urashima et al.: *Milk Oligosaccharides*. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyl-lactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments, a synthetic composition may be, but preferably is not, identical with a naturally occurring composition.

The synthetic composition typically comprises one or more HMOs but may include other substances such as probiotics, prebiotics, ketogenic compounds, excipients and the like. Some non-limiting embodiments of a synthetic composition of the invention are described below.

"Microbiota", "microflora" and "microbiome" mean a community of living microorganisms that typically inhabits a bodily organ or part, particularly the gastro-intestinal organs of humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria*, and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which are in or attached to the mucous layer covering the epithelium of the gastrointestinal tract, and luminal-associated microbiota, which is found in the lumen of the gastrointestinal tract.

"Enteral administration" means any conventional form for delivery of a composition to a human that causes the deposition of the composition in the gastrointestinal tract (including the stomach). Methods of enteral administration include feeding through a naso-gastric tube or jejunum tube, oral, sublingual and rectal.

"Oral administration" means any conventional form for the delivery of a composition to a human through the mouth. Accordingly, oral administration is a form of enteral administration.

"Effective amount" means an amount of a composition that provides an HMO in a sufficient amount to render a desired treatment outcome in a human. An effective amount can be administered in one or more doses to achieve the desired treatment outcome.

"Relative abundance of a *Bifidobacterium longum* and/or *Bifidobacterium bifidum*" means the abundance of a *Bifidobacterium longum* and/or *Bifidobacterium bifidum* relative to other bifidobacteria in the microbiota of the gastro-intestinal tract of ASD patients.

"Relative growth of a *Bifidobacterium longum* and/or *Bifidobacterium bifidum*" means the growth of a *Bifidobacterium longum* and/or *Bifidobacterium bifidum* relative to other bifidobacteria in the microbiota in the gastro-intestinal tract of patient humans.

"*Bifidobacterium* of the *B. adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. Appl. Environ. Microbiol. 79, 336 (2013), Bottacini et al. Microbial Cell Fact. 13:S4 (2014)). Preferably a *Bifidobacterium* of the *B. adolescentis* phylogenetic group is *Bifidobacterium adolescentis* and/or *Bifidobacterium pseudocatenulatum*.

"Relative abundance of a *Bifidobacterium* of the *B. adolescentis* phylogenetic group" means the abundance of a *Bifidobacterium* of the *B. adolescentis* phylogenetic group relative to other bifidobacteria in the microbiota of the gastro-intestinal tract of patients.

"Relative abundance of *B. adolescentis* and/or *B. pseudocatenulatum*" means the abundance of *B. adolescentis* and/or *B. pseudocatenulatum* relative to other bifidobacteria in the microbiota of the gastro-intestinal tract of patients.

"Relative growth of a *Bifidobacterium* of the *B. adolescentis* phylogenetic group" means the growth of a *Bifidobacterium* of the *B. adolescentis* phylogenetic group relative to other bifidobacteria in the microbiota in the gastro-intestinal tract of patients.

"Relative growth of *B. adolescentis* and/or *B. pseudocatenulatum*" means the growth of *B. adolescentis* and/or *B. pseudocatenulatum* relative to other bifidobacteria in the microbiota in the gastro-intestinal tract of patients.

"Treat" means to address a medical condition or disease with the objective of improving or stabilising an outcome in the person being treated. Treat includes the dietary or nutritional management of the medical condition or disease by addressing nutritional needs of the person being treated. "Treating" and "treatment" have grammatically corresponding meanings.

The term "dietary management" means exclusive or partial feeding of patients who, because of a disease, disorder or medical condition they are suffering from:
   either have a limited, impaired or disturbed capacity to take, digest, absorb, metabolise or excrete ordinary food or certain nutrients contained therein, or metabolites, or
   have other medically-determined nutrient requirements (see: Commission Notice on the classification of Food for Special Medical Purposes of the European Commission, *Official Journal of the European Union* C 401, 25 Nov. 2017, p. 10-11).

This invention is based on the finding that administration of one or more human milk oligosaccharides (HMOs) to autism spectrum disorder patients decreases the concentration of detrimental and/or proteolytic metabolites such as ammonia and branched chain fatty acids in the gastrointestinal tract of these patients. This in turn may result over time in an improvement in ASD symptom severity; for example, an at least a 10% reduction in ASD symptom severity after consumption of HMOs as compared to before initiating consumptions of HMOs; more preferably at least 20%. Further the administration of the one or more HMOs may result in improvement of GI symptoms; for example, at least a 20% improvement in GSRS score; more preferably at least 40%.

Accordingly, the first aspect of the invention relates to an HMO, advantageously a neutral HMO, for use in for use in:
   decreasing the concentration of proteolytic metabolites, such as ammonia and branched short chain fatty acids, in the gastro-intestinal tract of an autism spectrum disorder (ASD) patient;
   reducing gastrointestinal symptom severity in an ASD patient;
   improving gut barrier function in an ASD patient, and/or
   decreasing autism spectrum symptom severity in an ASD patient.

The HMO can be a neutral HMO or an acidic HMO, or a mixture of both. The neutral HMO is in one embodiment one or more fucosylated HMOs; in another embodiment, the HMO is one or more non-fucosylated HMOs. In one embodiment, the neutral HMO is a mixture neutral HMOs, preferably a mixture comprising or consisting of a fucosylated and a non-fucosylated neutral HMO. Particularly, the mixture contains or consists of one or more fucosylated neutral HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, preferably, at least 2'-FL, and a non-fucosylated neutral HMO selected from the list consisting of LNT, LNnT, LNH, LNnH, pLNH and pLNnH, e.g. LNnT. In some preferred embodiment, the mixture contains or consists of a fucosylated neutral HMO selected from the list consisting of 2'-FL, 3-FL and DFL, and a non-fucosylated neutral HMO selected from the list consisting of LNT and LNnT, advantageously the mixture comprises or consists of i) 2'-FL and/or DFL and ii) LNnT and/or LNT (meaning that the mixture comprises or consists of at least one of 2'-FL and DFL, and at least one of LNnT and LNT, for example a mixture comprising or consisting of 2'-FL and LNnT). The mixture can also be that containing or consisting of 2'-FL and DFL. The acidic HMOs are preferably selected from 3'-SL and 6'-SL.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified E. coli.

The second aspect of this invention is a synthetic composition comprising an HMO, preferably a neutral HMO or a mixture of neutral HMOs, even more preferably a mixture of a fucosylated and a non-fucosylated neutral HMOs as disclosed above in the first aspect, for use in:
- decreasing the concentration of proteolytic metabolites, such as ammonia and branched short chain fatty acids, in the gastro-intestinal tract of an autism spectrum disorder (ASD) patient;
- reducing gastrointestinal symptom severity in an ASD patient;
- improving gut barrier function in an ASD patient, and/or decreasing autism spectrum symptom severity in an ASD patient.

The synthetic composition can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted is reaction when administered to patients. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated to provide sustained, delayed or controlled release of the mixture therein.

The pharmaceutical compositions can also be administered by rectal suppository, aerosol tube, naso-gastric tube or direct infusion into the GI tract.

The pharmaceutical compositions can also include therapeutic agents such as antiviral agents, antibiotics, probiotics, analgesics, and anti-inflammatory agents. Further the pharmaceutical composition can include a ketogenic compound. Suitable ketogenic compounds include medium chain triglycerides and hydroxycarboxylic esters, especially monoesters with an alkanediol. Examples of suitable ketogenic compounds include hydroxybutyrates and their derivatives, for example esters of hydroxybutyrate including (R)-3-hydroxybutyrate and derivatives, esters of (R)-3-hydroxybutyrate and oligomers of (R)-3-hydroxybutyrate including esters derived from alcohols and compounds containing one or more free hydroxyl groups. Suitable alcohols include butanediol, especially, butane-1,3-diol, altrose, arabinose, dextrose, erythrose, fructose, galactose, glucose, glycerol, gulose, idose, lactose, lyxose, mannose, ribitol, ribose, ribulose, sucrose, talose, threose, xylitol, xylose. In an especially preferred embodiment, the ketogenic compound is a medium chain triglyceride or D-β-hydroxybutyrate-(R)-1,3-butanediol monoester ((R)-3-hydroxybutyl (R)-3-hydroxybutyrate), or both. The ketogenic compound raises the concentration of ketone bodies in the patient, potentially improving mitochondrial function and autism spectrum symptom severity.

The proper dosage of the pharmaceutical composition for an ASD patient can be determined in a conventional manner, based upon factors such immune status, body weight and age. In some cases, the dosage will be at a concentration similar to that found for the HMOs in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by conventional methods. Ideally, a dose of about 2 g to about 10 g per day is administered; for example 3 g to 10 g or 3 g to 7.5 g.

The synthetic composition can also be a nutritional composition. It can contain sources of protein, lipids and/or digestible carbohydrates and can be in powdered or liquid forms. The composition can be designed to be the sole source of nutrition or a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for ASD patients with inflamed GI tracts. The protein can also be provided in the form of free amino acids; especially ketogenic amino acids. The protein can comprise about 5% to about 30% of the energy of the nutritional composition when the composition is the sole source of nutrition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve the intestinal barrier.

Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from lactose. Generally digestible carbohydrates provide about 35% to about 55% of the energy of the nutritional composition when the composition is the sole source of nutrition. Preferably the nutritional composition is free from lactose. A particularly suitable digestible carbohydrate is a low dextrose equivalent (DE) maltodextrin. Digestible carbohydrates may also provide a minimal amount of the energy of the nutritional composition; for example, less than about 10%; especially if the composition is intended to place the ASD patient in a state of ketosis.

Suitable lipids include medium chain triglycerides (MCT) and long chain triglycerides (LCT). In one embodiment, the lipid is a mixture of MCTs and LCTs. For example, MCTs can comprise about 30% to about 70% by weight of the lipids, more specifically about 50% to about 60% by weight. MCTs offer the advantage of easier digestion which can be important for ASD patients with inflamed GI tracts. The lipids can also comprise substantially only MCTs. Generally, the lipids provide about 35% to about 50% of the energy of the nutritional composition when the composition is the sole source of nutrition. However, if the lipids are intended to be a significant source of ketogenic compounds, the lipids can provide greater than 50% of the energy of the nutritional composition; for example, from about 50% to 99% of the energy of the composition. The lipids can also contain essential fatty acids (omega-3 and omega-6 fatty acids). Preferably these polyunsaturated fatty acids provide less than about 30% of total energy of the lipid source. Decreasing the levels of these polyunsaturated fatty acids is believed to decrease sensitivity to peroxidation; which can be beneficial for ASD patients having inflammatory conditions.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n−6) to omega-3 (n−3) ratio of about 4:1 to about 10:1. For example, the n−6 to n−3 fatty acid ratio can be about 6:1 to about 9:1.

The nutritional composition preferably also includes vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HN019, *B. lactis* Bi07, *B. infantis* ATCC 15697, *L. rhamnosus* GG, *L. rhamnosus* HNOOI, *L. acidophilus* LA-5, *L. acidophilus* NCFM, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can also include a ketogenic compound as described above.

The nutritional composition can be in the form of a soluble powder, a liquid concentrate, or a ready-to-use formulation. The composition can be fed to a ASD patient via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, the total concentration of HMOs in the liquid, by weight of the liquid, is from about 0.0001% to about 2.0%, including from about 0.001% to about 1.5%, including from about 0.01% to about 1.0%. When the nutritional product is a concentrated nutritional liquid, the total concentration of HMOs in the liquid, by weight of the liquid, is from about 0.0002% to about 4.0%, including from about 0.002% to about 3.0%, including from about 0.02% to about 2.0%.

The synthetic composition, preferably the nutritional composition, can also be in a unit dosage form such as a capsule, tablet or sachet/stick pack. For example, the synthetic composition, preferably the nutritional composition, can be in a tablet form or powder form comprising the HMOs, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methylacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet/stick pack form, can also include various nutrients including macronutrients.

The proper dosage of the nutritional composition for an ASD patient can be determined in a conventional manner, based upon factors such immune status, body weight and age. In some cases, the dosage will be at a concentration similar to that found for the HMOs in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by conventional methods. Ideally, a dose of about 3 g to about 10 g per day is administered.

The HMO or synthetic composition can be presented in the form of a pack comprising at least 7 individual daily doses of an effective amount of the human milk oligosaccharide. The daily doses are preferably in sachet/stick pack form but may be in any suitable form. Each dose preferably contains about 1 g to about 20 g of the human milk oligosaccharide, more preferably about 2 g to about 10 g, for example about 3 g to about 7.5 g. Preferably, the pack comprises at least 14 daily doses; more preferably at least 21 daily doses. Most suitable packs contain sufficient for 4 weeks or a full month. The pack can include instructions for use.

The HMOs, synthetic composition and pack can be used in a method for:
  decreasing the concentration of proteolytic metabolites, such as ammonia and branched short chain fatty acids, in the gastro-intestinal tract of an ASD patient;
  reducing gastrointestinal symptom severity in an ASD patient;
  improving gut barrier function in an ASD patient and/or decreasing autism spectrum symptom severity in an ASD patient.

In one embodiment, the method is useful for:
  decreasing the concentration of proteolytic metabolites, such as ammonia and branched short chain fatty acids, in the gastro-intestinal tract of an ASD patient;
  reducing gastrointestinal symptom severity in an ASD patient; and or
  improving gut barrier function in an ASD patient.

An appropriate dose to be used in the method can be determined based on several factors, including, for example, body weight and/or condition, the severity of gastrointestinal symptoms, the incidence and/or severity of side effects and the manner of administration. Appropriate dose ranges may be determined by methods known to those skilled in the art. During an initial treatment phase, the dosing can be higher (for example 200 mg to 20 g per day, preferably 500 mg to 15 g per day, more preferably 1 g to 10 g per day, in certain embodiments 3 g to 7.5 g per day). During a maintenance phase, the dosing can be reduced (for example, 10 mg to 10 g per day, preferably 100 mg to 7.5 g per day, more preferably 500 mg to 5 g per day, in certain embodiments 1 g to 2.5 g or 1 g to 3 g per day).

The duration of treatment can be determined based on several factors, including, for example, body weight and/or condition, the severity of gastrointestinal symptoms, the incidence and/or severity of side effects. Preferably, the duration is at least 14 days, more preferably at least 4 weeks. The synthetic composition or HMOs may also be taken chronically.

A certain aspect of the invention is a use of
  one or more human milk oligosaccharides (HMOs), advantageously a neutral HMO,
  a synthetic composition comprising one or more human milk oligosaccharides (HMOs), advantageously a neutral HMO, or
  a pack comprising at least 7 individual daily doses of an effective amount of one or more human milk oligosaccharides, advantageously a neutral HMO,
in the dietary management of an ADS patient.

The ADS patient, in some embodiments, has
  an increased concentration of detrimental proteolytic metabolites, such as ammonia and branched short chain fatty acids, in the gastro-intestinal tract, and/or a disease associated with an increased concentration of detrimental proteolytic metabolites, such as ammonia and branched short chain fatty acids, in the gastrointestinal tract.

EXAMPLES

The working example described herein are for illustration purposes only and should not be considered as limiting.

Example 1

The impact of the HMOs on microbiota and bacterial metabolites was investigated in the M-SHIME® (M-TripleSHIME®) in vitro gastrointestinal model (Prodigest). The typical reactor setup of the M-TripleSHIME® consisted of a succession of four reactors simulating the different parts of the human gastrointestinal tract. The first two reactors were of the fill-and-draw principle to simulate different steps in food uptake and digestion, with peristaltic pumps adding a defined amount of SHIME feed (140 mL 3×/day) and pancreatic and bile liquid (60 ml 3×/day), respectively, to the stomach and small intestine compartment and emptying the respective reactors after specified intervals. The last two compartments were continuously stirred reactors with constant volume and pH control. The retention time and pH of the different vessels were chosen to resemble in vivo conditions in the different parts of the colon. The proximal colon was set to pH 5.4-5.6 and retention time=12 h, and the distal colon was set to pH 6.0-6.5 and retention time=20 h. 2'-FL, LNnT or Mix (2'-FL:LNnT in 4:1 weight ratio) was added to the SHIME feed in a concentration that equalled 10 gram per day. Upon inoculation with faecal microbiota, these reactors simulated the ascending and descending colon. After a two-week adaptation of the microbial communities in the different regions of the colon, a representative microbial community was established in the colon compartments, which differed both in composition and functionality in the different colon regions.

Further, porcine mucin capsules were included in the reactors simulating the colon to take into account the colonisation of the mucous layer. Thus the M-SHIME® permitted culturing both the luminal and mucous-associated microbial community over periods of several weeks.

The M-TripleSHIME® was run in four stages:
1. Stabilisation: After inoculation of the reactors with a fresh faecal sample taken from a healthy adult, a two-week stabilisation period allowed the microbial community to differentiate in the different reactors depending on the local environmental conditions. During this period the basic nutritional matrix was provided to support the maximum diversity of the gut microbiota originally present in the faecal inoculum.
2. Control: During this two-week period, a standard nutrient matrix was dosed into the model for a period of 14 days. The baseline microbial community composition and activity in the different reactors was determined by analysis of samples and was used as a reference.
3. Treatment: The SHIME system was operated under normal conditions for 3 weeks, but with the standard nutrient matrix supplemented with the HMOs. The HMOs tested were 2'-FL, LNnT and a 4:1 mix of 2'-FL and LNnT.
4. Washout: During this two-week period, the SHIME system was again run with the standard nutrient matrix only.

Sample of the liquids in each reactor were collected regularly (three times in a week, on day 1, day 3 and day 5) and were analysed for microbial metabolites and the composition of the resident microbial community. In particular, the bifidobacteria composition was analysed using ITS profiling.

The results from the fermentation system showed that HMOs impacted the base-acid consumption meaning that HMOs were fermented both in the proximal colon and, to a lesser extent, the distal colon. The profiling of the *Bifidobacterium* community showed that, for the first 2 weeks, the abundance of *B. adolescentis* increased when consuming HMOs. However, by week 3, the relative abundance of members of the *B. adolescentis* phylogenetic group reduced while the abundance and relative abundance of *Bifidobacterium longum* and/or *Bifidobacterium bifidum* increased. Additionally, the relative abundance of proteolytic bacteria was decreased and butyrate-producing bacteria within the Lachnospiracea family were increased.

FIG. 1 shows the effect of 2'-FL on branched SCFA and ammonia production (mg/l) in the proximal (PC) and distal (DC) colon reactor. The values plotted are means of the three weekly samples. The results of the tests concerning LNnT or the mixture of 2'-FL:LNnT are similar.

The bacterial metabolite analysis showed that HMO treatment induced an immediate increase in total SCFA production in both colon regions, mainly due to increase in the production of acetate and propionate. During the third week of HMO treatment, butyrate was increased. Additionally, the analysis showed that ammonia and branched short chain fatty acids was decreased during treatment with the HMOs in both the proximal and distal colon.

HMOs shift the bacterial community leading to a beneficial shift in the bacterial metabolism from a proteolytic to a saccharolytic metabolism; reducing ammonia concentrations and branched short chain fatty acids, and increasing butyrate.

Example 2

A total of 100 male and female healthy adults are recruited to participate in the study. After a screening visit and run-in period of 1-2 weeks, the participants are selected and randomized into ten groups, each of 10 subjects. One group is administered a placebo product containing 2 grams of glucose. The remaining 9 groups are administered treatment product containing a) 20 g of 2'-FL, b) 10 g of 2'-FL, c) 5 g of 2'-FL, d) 20 g of LNnT, e) 10 g of LNnT, f) 5 g of LNnT, g) 20 g of a 2:1 mixture (by weight) of 2'-FL and LNnT, h) 10 g of a 2:1 mixture (by weight) of 2'-FL and LNnT, and i) 5 g of a 2:1 mixture (by weight) of 2'-FL and LNnT for 4 weeks. The placebo and treatment products are in powder form in a unit dosage container.

The healthy adults are eligible to participate if they are at an age between 18-60 years. All recruited participants are able and willing to understand and comply with the study procedures. Participants are excluded if: they had participated in a clinical study one month prior to screening visit; they had abnormal results in the screening tests which were clinically relevant for study participation; they are suffering for a severe disease such as malignancy, diabetes, severe coronary disease, kidney disease, neurological disease, or severe psychiatric disease or any condition which could confound the results of the study; used highly dosed probiotic supplements (yoghurt allowed) for 3 months prior to the study; they consumed antibiotic drugs 6 months prior to the study; they consumed on a regular basis any medication that might have interfered with symptom evaluation 2 weeks prior to the study; and are pregnant or lactating.

At the screening visit, medical history and concomitant medication is registered and a blood sample for safety analyses is collected. A faecal sample kit is distributed. Participants are instructed to keep their samples in the freezer until the next visit.

At the second visit, eligibility criteria are checked and eligible subjects are randomised to the ten arms in the trial (treatment groups and placebo group). The faecal samples are collected and equipment for new samples are distributed. Participants are familiarised with an interactive internet enabled system which recorded data daily and are provided with either treatment or control products. Subjects are reminded not to change their usual diet during the study. Blood samples are collected for biomarker studies. The faecal samples are stored at −80° C. until analysis.

The study runs for 4 weeks with the participants consuming either a placebo or a treatment product daily. Participants are instructed to consume the products in the morning with breakfast. Compliance is monitored through the interactive internet enabled system.

The participants also use the system to record:
Bristol Stool Form Scale (BSFS) information.
Symptom information such as abdominal pain, abdominal discomfort, abdominal cramping, abdominal bloating, and abdominal fullness.
Additional, Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

After 2 weeks, each participant has a visit with the medical team. Faecal samples and blood samples are collected. The faecal samples are stored at −80° C. until analysis. Equipment for new samples are distributed. Subjects are reminded not to change their usual diet during the study.

After 4 weeks, each participant has an exit visit with the medical team. Faecal samples and blood samples are collected. The faecal samples are stored at −80° C. until analysis.

Blood samples are analysed simultaneously in a multiplexing format on an electro chemiluminescence platform. The following analytes are included in the panel: BUN, LDL cholesterol, HDL cholesterol, iron, triglycerides, ApoA1, ApoB, insulin, FFAs, glucagon, IL-10, IL-6 and TNF-α.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al. *Nucleic Acids Res.* 41, e1 (2013)). These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, *Nature Methods* 10, 996 (2013)) is used for bioinformatical analysis of the sequence data.

To assess the *Bifidobacterium* community, ITS profiling of DNA samples is performed.

The results from the profiling of the *Bifidobacterium* community shows that, for the first 2 weeks, the abundance of *B. adolescentis* increases when consuming a single HMO, where the abundance of *B. pseudocatenulatum* increases when consuming a mix of two HMOs. Both *B. adolescentis* and *B. pseudocatenulatum* are members of the *B. adolescentis* phylogenetic group. At 4 weeks, the abundance of members of the *B. adolescentis* phylogenetic group reduce while the abundance of *Bifidobacterium longum* and/or *Bifidobacterium bifidum* increase. Oral ingestion of the HMOs for more than 14 days clearly increases the abundance of *Bifidobacterium longum* and/or *Bifidobacterium bifidum* in the microbiota of healthy adults, as well as their relative abundance compared to the totality of other *Bifidobacterium* species. Proteolytic metabolites, such as ammonia and branched chain fatty acids, decrease and butyrate increases.

Example 3

20 autistic children, ages 7-17, are recruited to participate in a trial. At a screening visit, the participants are diagnosed with ASD using the Autism Diagnostic Interview-Revised (ADI-R).

Participants are excluded if they have consumed antibiotics in last 3 months and probiotic supplements in last month, have single-gene disorder, have major brain malformation, have GI diseases such as Ulcerative Colitis, Crohn's disease, Celiac Disease, Eosinophilic Gastroenteritis, are severely underweight/malnourished. All participants have moderate to high cognitive functioning. Further medical history and concomitant medication is registered and a blood sample for safety analyses is collected. A faecal sample kit is distributed. Participants are instructed to keep their samples in the freezer until the next visit.

Each child participates in the study for 12 weeks in total. At visit 1, eligibility criteria are checked. The faecal samples are collected and equipment for new samples are distributed. Blood samples are collected for biomarker studies. The faecal samples are stored at −80° C. until analysis. Further each child under goes the following base line assessments:
Autism Diagnostic Interview-Revised (ADI-R) to verify the diagnosis of ASD for admission into the study. It is not designed to be a measure of autism severity, but higher scores are generally consistent with more severe symptoms.
Childhood Autism Rating Scale (CARS) is a 15-item scale to verify the diagnosis of ASD and to assess the overall severity of symptoms.
Aberrant Behaviour Checklist (ABC) to assess problem behaviours in five areas common in children with ASD, including irritability, lethargy, stereotypy, hyperactivity, and inappropriate speech.
Social Responsiveness Scale (SRS) is a 65-item scale to assess social impairments, a core issue in autism, including social awareness, social information processing, capacity for reciprocal social communication, social anxiety/avoidance, and autistic preoccupations and traits.

Vineland Adaptive Behaviour Scale II (VABS-II) to measure functioning level in four different domains: Communication, Daily Living Skills, Socialization, and Motor Skills, and 11 sub-domains. The raw scores are converted into an age equivalent score.

The GSRS to assess 15 gastrointestinal symptoms covering five dimensions (abdominal pain, indigestion, reflux, diarrhoea, constipation) using a seven-graded Likert scale.

The Bristol Stool Form Scale (BSFS) to assess faecal consistency.

Each participant then commences orally consuming a nutritional product containing 5 g of a 4:1 mixture (by weight) of 2'-FL and LNnT. The product is in powder form in a unit dosage container. The administration continues daily for 12 weeks. Each participant has further visits at 4 weeks, 8 weeks and 12 weeks. At each visit, faecal samples are collected and, except for the 12-week visit, equipment for new samples is distributed. Blood samples are taken at the 12-week visit. The faecal samples are stored at 80° C. until analysis. Further each child under goes the following assessments: —ADI-R, CARS, ABC, SRS, VABS-II, GSRS and BSFS assessments. At the 12-week visit, the parents are asked to complete the Parent Global Impressions—III assessment to evaluate changes in 17 scales, and overall, using a 7-point scale ranging from "much worse" to "much better". An "Average Change" is computed by computing the average in all 18 scores.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al. *Nucleic Acids Res.* 41, e1 (2013)). These are universal bacterial 16S rDNA primers, which targeted the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, *Nature Methods* 10, 996 (2013)) is used for bioinformatical analysis of the sequence data.

To assess the *Bifidobacterium* community, ITS profiling of DNA samples is performed. The results from the profiling of the *Bifidobacterium* community shows the abundance of *Bifidobacterium longum* and/or *Bifidobacterium bifidum* increase at 4 weeks, 8 weeks and 12 weeks as compared to base-line. Further the relative abundance compared to the totality of other *Bifidobacterium* species increases at 4 weeks, 8 weeks and 12 weeks as compared to base-line. The ammonia concentration in faeces is reduced compared to base line at 4 weeks, 8 weeks and 12 weeks. Further butyrate concentrations in faeces are increased compared to base line at 4 weeks, 8 weeks and 12 weeks.

The GSRS assessment indicates an improvement of gastrointestinal symptoms by 4 weeks which is maintained until 12 weeks. Similarly, the BSFS assessment indicates reduced abnormal stool.

The assessment of Autism Symptoms indicates an improvement of autism symptoms by 4 weeks which is maintained until 12 weeks.

The invention claimed is:

1. A method comprising:
    selecting a non-infant human with autism spectrum disorder and one or more associated symptoms selected from neurobehavioral symptoms, gastrointestinal symptoms, and combinations thereof;
    selecting an effective amount of one or more synthetic human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount of chosen HMOs effective for increasing a relative abundance of *Bifidobacterium adolescentis* in the gastrointestinal microbiota of a non-infant human;
    shifting the gastrointestinal microbiota of the non-infant human away from a proteolytic metabolism toward a saccharolytic metabolism by increasing the relative abundance of *Bifidobacterium adolescentis* in the gastrointestinal microbiota of the non-infant human and causing a delayed increase of butyrate in colon of the non-infant human by administering the effective amount of the chosen HMOs to the non-infant human, wherein during an initial treatment phase, the effective amount is a daily dosage for non-infants of from about 3 g to about 10 g per day; and
    reducing frequency and/or severity of the one or more symptoms associated with the autism spectrum disorder ("ASD") in the non-infant human by administering the effective amount of the chosen HMOs to the non-infant human.

2. The method of claim 1, wherein the one or more chosen synthetic HMOs consist of a mixture of one or more neutral fucosylated HMOs selected from 2'-FL, 3-FL, DFL, and LNFP-I, and one or more neutral non-fucosylated HMOs selected from LNT and LNnT.

3. The method of claim 2, wherein the mixture includes at least 2'FL and LNnT.

4. The method of claim 1, further comprising reducing a concentration of detrimental proteolytic metabolites in the blood and/or feces of the non-infant human.

5. The method of claim 1, wherein the detrimental proteolytic metabolites in the gastrointestinal tract of the non-infant human are selected from ammonia, branch short-chain fatty acids, and combinations thereof.

6. The method of claim 1, wherein the concentration of ammonia in the gastrointestinal tract of the non-infant human is reduced by at least 10% relative to the concentration of ammonia in the gastrointestinal tract of the non-infant human prior to the administration of the composition.

7. The method of claim 1, wherein the concentration of short-chain branch fatty acids in the gastrointestinal tract of the non-infant human is reduced by at least 10% relative to the concentration of branch short-chain fatty acids in the gastrointestinal tract of the non-infant human prior to the administration of the composition.

8. The method of claim 1, wherein the delayed increase in the concentration of butyrate in the gastrointestinal tract of the non-infant human comprises an increase of at least 50% relative to the concentration of butyrate in the gastrointestinal tract of the non-infant human prior to the treatment period.

9. The method of claim 1, further comprising administering a ketogenic compound with the selected effective amount of the chosen synthetic HMOs to the non-infant human.

10. The method of claim 9, wherein the ketogenic compound is selected from a medium-chain triglyceride, a ketone body, and combinations thereof.

11. A method comprising:
selecting a non-infant human with autism spectrum disorder and one or more associated symptoms selected from neurobehavioral symptoms, gastrointestinal symptoms, and combinations thereof;
selecting an effective amount of one or more synthetic human milk oligosaccharides (HMOs) chosen from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount of chosen HMOs effective for increasing a relative abundance of *Bifidobacterium adolescentis* in the gastrointestinal microbiota of a non-infant human;
shifting the gastrointestinal microbiota of the non-infant human away from a proteolytic metabolism toward a saccharolytic metabolism by increasing the relative abundance of *Bifidobacterium adolescentis* in the gastrointestinal microbiota of the non-infant human and causing a delayed increase of butyrate in the colon of the non-infant human by enterally administering the effective amount of the chosen HMOs to the non-infant human, wherein during an initial treatment phase, the effective amount is a daily dosage for non-infants of from about 3 g to about 10 g per day; and
reducing the one or more neurobehavioral symptoms of the autism spectrum disorder and reducing gastrointestinal symptom severity or improving gut barrier function in the non-infant human by administering the selected effective amount of the chosen HMOs.

12. The method of claim 11, further comprising decreasing a concentration of proteolytic metabolites selected from ammonia, branched short chain fatty acids, and combinations thereof in the gastrointestinal tract of the non-infant human.

13. The method of claim 11, wherein the gastrointestinal symptom severity is reduced by at least 20% as assessed by the Gastrointestinal Symptom Rating Scale (GSRS) relative to severity as assessed prior to administration of the composition.

14. The method of claim 13, further comprising reducing symptom severity of one or more symptoms associated with ASD in the non-infant human.

15. A method comprising:
selecting a non-infant human with autism spectrum disorder and one or more gastrointestinal symptoms associated with gut dysbiosis;
selecting an effective amount consisting of at least one synthetic human milk oligosaccharide ("HMO") selected from 2'-FL, 3-FL, DFL, LNnT, LNT, and mixtures thereof, the selected amount effective to increase the relative abundance of *Bifidobacterium adolescentis* in the gastrointestinal microbiota of the non-infant human, wherein during an initial treatment phase, the effective amount is a daily dosage for non-infants of from about 3 g to about 10 g per day;
shifting the gastrointestinal microbiota of the non-infant human away from a proteolytic metabolism toward a saccharolytic metabolism by increasing the relative abundance of *Bifidobacterium adolescentis* in the gastrointestinal microbiota of the non-infant human and causing a delayed increase of butyrate in colon of the non-infant human by administering the effective amount of the chosen HMOs to the non-infant human;
reducing by at least 10 percent, a concentration of at least one detrimental proteolytic metabolite selected from ammonia and branched short-chain fatty acids, in the gastrointestinal tract of the non-infant human relative to a concentration of the at least one detrimental proteolytic metabolite prior to the administration of the composition; and
reducing severity and/or frequency of one or more autism spectrum symptoms in the non-infant human.

16. The method of claim 15, wherein the one or more autism spectrum symptoms reduced comprise one or more gastrointestinal symptoms and one or more neurobehavioral symptoms.

17. The method of claim 16, wherein the one or more synthetic neutral HMOs chosen are selected from 2'-FL, LNnT or the combination thereof.

18. The method of claim 17, wherein the initial treatment phase is at least 2 weeks.

19. The method of claim 18, further comprising administering a reduced daily dosage of the chosen HMOs during a maintenance treatment phase of from 500 mg to 5 g per day following the initial treatment phase.

20. The method of claim 19, further comprising increasing the concentration of butyrate in the gastrointestinal tract of the non-infant human by at least 50% relative to the concentration of butyrate in the gastrointestinal tract of the non-infant human prior to the first treatment period.

* * * * *